United States Patent [19]

Suddath

[11] Patent Number: 5,456,126
[45] Date of Patent: Oct. 10, 1995

[54] FLUID VALVE AND GAS SAMPLE CONTAINER USING SAME

[75] Inventor: James N. Suddath, West Bloomfield, Mich.

[73] Assignee: Bellaire Industries, Inc., Royal Oak, Mich.

[21] Appl. No.: 210,922

[22] Filed: Mar. 21, 1994

[51] Int. Cl.⁶ .................................................. G01N 1/12
[52] U.S. Cl. ................................... 73/864.63; 73/864.62; 73/864.91
[58] Field of Search ............................ 73/23.31, 864.62, 73/863.72, 863.84, 863.86, 864.63, 864.91; 251/61, 61.1

[56] References Cited

U.S. PATENT DOCUMENTS

| | | |
|---|---|---|
| 3,087,339 | 4/1994 | Henderson ........................ 73/863.84 |
| 3,374,660 | 3/1968 | McKinney et al. . |
| 3,581,573 | 6/1971 | Purcell . |
| 4,262,880 | 4/1981 | Danko et al. . |
| 4,463,603 | 8/1984 | Welker ........................... 73/864.62 |
| 4,915,356 | 4/1990 | Guild et al. . |
| 5,074,155 | 12/1991 | Vecere . |
| 5,095,765 | 3/1992 | Filbey et al. ..................... 73/863.86 |
| 5,105,653 | 4/1992 | Konter ............................ 73/756 |
| 5,218,874 | 6/1993 | Vecere . |
| 5,239,877 | 8/1993 | Suddath et al. . |

Primary Examiner—Richard E. Chilcot, Jr.
Assistant Examiner—Max H. Noori
Attorney, Agent, or Firm—Basile and Hanlon

[57] ABSTRACT

A body has a through bore with first and second ends and an intermediate disposed transverse bore extending through a side wall in fluid flow communication with the through bore. A flow control member with a first transverse bore is movably mounted on the body. The flow control member is movable from a first position in which the first transverse bore is aligned with the transverse bore in the body to form a fluid flow path therethrough to a container attached to one end of the body, and a second position in which the first transverse bore is offset from the transverse bore in the body to block fluid flow through the body. A septum, mounted in the second end of the through bore of the body, is pierceable by a syringe to withdraw or inject quantities of gas from or into the container attached to the body. A clamp ring is mountable over the first end of the body and sealingly traps edges of the side wall of the container surrounding an aperture in the side wall of the container to sealingly attach the body to the container. Detents and mating projections are formed in the flow control member and the clamp ring to define the closed position of the flow control member. Mating projections and annular ridges on the flow control member and the clamp ring define the fluid flow open positions of the valve upon rotation of the flow control member.

65 Claims, 5 Drawing Sheets

FLUID VALVE AND GAS SAMPLE CONTAINER USING SAME

BACKGROUND OF THE INVENTION

1. Field of the Invention

The present invention relates, in general, to valves for controlling fluid flow into and out of containers and, specifically, to valves and fittings for controlling fluid flow into and out of gas sample containers.

2. Description of the Art

Expandable, sealed containers or bags are employed for collecting and temporarily storing gas emissions from various sources such as air, smokestack discharge, effluent and motor vehicles. The containers are then connected to suitable test equipment, such as a gas chromatograph, for example, to test the gas stored in such container.

The expandable containers include a fitting sealingly mounted in each container which can alternately be connected to the gas source to receive gas emissions therefrom or to the test equipment for analyzing a previously collected gas sample stored within the container. The fitting directs the gas into the container for storage as well as enabling the stored gas contents to be evacuated from the container for subsequent analysis. The fitting and the sealed container are typically made of a chemically inert material, such as a fluorinated carbon plastic, i.e., plastic sold under the registered trademarks TEFLON, KYNAR, and/or TEDLAR.

Frequently minute amounts of gas, i.e., 5 to 10 ml, are withdrawn from the container stored in a gas sample container. The valves or fittings previously used with motor vehicle gas emission sample containers are movable between fully closed and fully opened positions and discharge large quantities of gas from the containers when opened. This prohibits any subsequent testing of the gas remaining in the container since it is impossible to discharge only a minute quantity from the container.

U.S. Pat. No. 4,915,356 discloses a valve for controlling fluid flow into and out of a container through an elastomeric flow control element which is disposed in the fluid flow path between the inlet and outlet of the valve. When the flow control element is moved to the flow blocking position between the inlet and outlet of the valve, a syringe can be inserted through the element to withdraw a minute quantity of gas from the container attached to the valve.

While this valve provides a means for sampling minute quantities of gas within a sealed container without discharging large quantities of gas from the container, the elastomeric flow control element is located in the main fluid flow path and movement of the flow control element by a surrounding collar opens and closes the valve. Such repeated opening and closing operations can cause wear of the flow control element which could lead to loss of its sealing characteristics.

Figure 10:
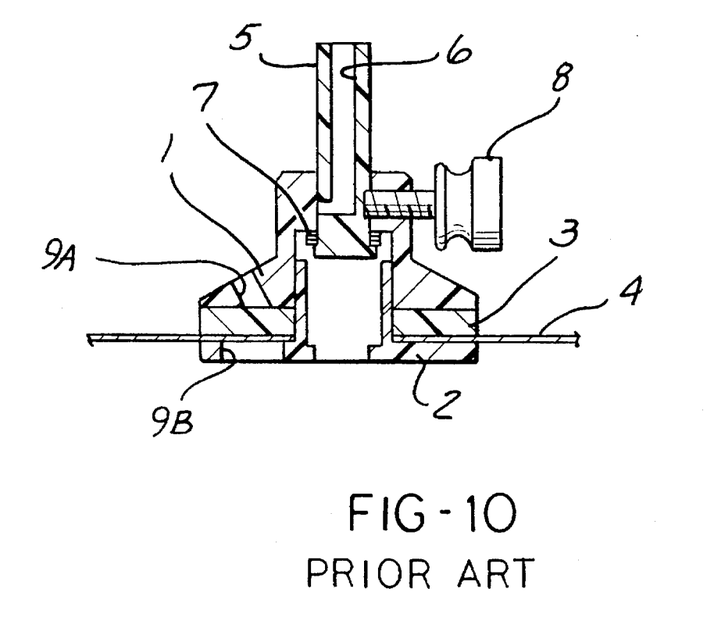
FIG. 10 is a cross sectional view of a prior art septum valve.

Another prior art valve manufactured by Welsh Fluorocarbon and used with sealed containers is shown in FIG. 10. This valve includes a body 1 having a through bore extending therethrough. An annular collar 2 has a centrally located, longitudinally extending, hollow tubular portion which is press fit into one end of the through bore in the body 1. A pierceable septum 3 is mounted between one end of the body 1 and the annular collar 2 in contact with a flexible sheet 4 which forms one side wall of a sealed container. An aperture is formed in the septum 3, the annular collar 2, and the flexible sheet 4, with the tubular portion of the annular collar 2 extending through the aperture in the flexible sheet 4.

An elongated stem 5 is slidably mounted in the bore of the body 1 and has a longitudinally extending bore 6 which terminates in an outlet port spaced from one end of the stem 5. An O-ring 7 is mounted on an annular disk slidably disposed about one end of the stem 5. A metallic washer is also disposed about the stem 5 and is located adjacent to the annular disk supporting the O-ring 7. A set screw 8 threadingly extends through the body and is engageable with the stem 5 to lock the stem 5 in the closed position shown in FIG. 10. In this position, the O-ring 7 sealingly engages an internal shoulder formed in the bore of the body 1 and closes off fluid flow through the bore 6 in the stem 5. The bore 6 in the stem 5 is in turn connected to an external conduit, not shown, for fluid flow through the valve to the sealed container as well as to evacuate the sealed container of fluid through the body 1 and stem 5.

To open the valve to fluid flow to and from the sealed container, the set screw 8 is unthreaded and the stem 5 is pushed into the body 1 until an enlarged end portion of the stem 5 engages an edge formed on the annular collar 2 surrounding the centrally located aperture therein. In this position, the outlet of the bore 6 in the stem 5 is open to the internal bore within the body 1 for the flow of fluid through the stem 6 into or out of the sealed container on which the valve is mounted.

A small diameter bore 9A is formed in one end of the body 1 and is aligned with a bore 9B formed in the annular collar 2. A syringe may be extended into the bore 9A, through the septum 3 and the bore 9B into the interior of the sealed container to withdraw minute quantities of gas stored within the sealed container. When the syringe is withdrawn, the septum 3, which is formed of a self-healing material, closes the opening formed by the syringe to seal off the interior chamber within the sealed container.

While this valve permits the withdrawal of minute quantities of gas from the sealed container on which the valve is mounted, it relies on a threaded set screw to lock the valve in the closed position. Due to the formation of the components of this valve from plastic, repeated opening and closing of the set screw results in wear of the engagement point between the set screw and the stem which, over time, can result in less than secure locking of the stem which could permit slight movement of the stem from the closed position and thereby prevent the stem from completely sealing the bore in the body.

Further, due to the formation of the stem in a single diameter, the stem can only be connected to a single sized conduit or external fitting thereby limiting the valve to only a single size external connection. Further, steel pins, not shown, are forced through the aligned portions of the body 1 and the centrally located tubular portion of the annular collar 2 to fixedly join the annular collar 2 to the body 1. Since it is difficult to remove the pins from the body 1 and the annular collar 2 without destroying the valve, this valve can only be used in a single application on a particular sealed container. If it is necessary to remove the valve from the sealed container, the entire valve must be completely replaced.

Thus, it would be desirable to provide a valve for a sealed gas container which overcomes the deficiencies found in previously devised valves of the same type. It would also be desirable to provide a valve for a sealed gas container which is easy to open and close while still providing an expedient means to remove minute quantities of gas from or inject gas into a sealed container attached thereto without discharging large quantities of gas from the container. It would also be desirable to provide a valve having these features which can be easily mounted on a sealed gas sample container. It would also be desirable to provide such a valve which can easily be detached from the container for reuse of the valve and the container. It would also be desirable to provide such a valve which is capable of receiving different size fittings. Finally, it would be desirable to provide such a valve which has multiple ports for separate fluid flow paths to the container.

SUMMARY OF THE INVENTION

The present invention is a valve for use with a sealed container, such as a gas sample container.

The valve includes a body having a fluid flow bore extending therethrough. A transverse bore is formed in the body and disposed in fluid flow communication with the fluid flow bore in the body. A flow control member is movably mounted on the body and has a first transverse bore extending therethrough. The flow control member is movable between a first position in which the first transverse bore is aligned with and disposed in fluid flow communication with the transverse bore in the body to form a fluid flow path through the body and the flow control member, and a second position in which the first transverse bore in the flow control member is offset from the transverse bore in the body to close off fluid flow through the body.

An annular O-ring is mounted in a groove formed on a side wall of the fitting body and concentrically surrounds the transverse bore in the fitting body. The O-ring forms a seal about the aligned transverse bores in the fitting body and the flow control member when the flow control member is rotated to an open, fluid flow position. In addition, the O-ring sealingly engages an inner face of the flow control member when the flow control member is rotated to a closed position to sealingly close off fluid flow through the valve.

A septum is mounted in the fluid flow bore in the body displaced from the transverse bore in the body. A first surface of the septum faces the fluid flow bore in the body. A septum retainer is provided for sealingly mounting the septum in the second end of the body. A bore extends through the septum retainer and opens to one surface of the septum to allow a syringe to be inserted therethrough to pierce the septum for the removal or injection of minute quantities of gas from or to the sealed container attached to the valve.

Mounting means are provided for mounting the valve body to a sealed container. In a preferred embodiment, the mounting means comprises a shoulder formed at an enlarged diameter end of the body. A clamp ring is slid over the body and has an internal shoulder formed therein which engages the shoulder formed between the side wall and the enlarged diameter end of the body to trap edges of a flexible sheet surrounding an aperture in one side wall of the sealed container therebetween, with the fluid flow bore in the body disposed in fluid flow communication with the interior of the container through the aperture in the container. A seal member is disposed between the internal shoulder of the clamp ring and the mating shoulder on the end of the body to sealingly close the aperture in the container.

Rotation limiting means are also provided on the flow control member and the clamp ring to control the angular movement of the flow control member between various defined positions. The rotation limiting means includes bosses formed at predetermined angular positions on the clamp ring which engage arcuate ridges extending from one end of the flow control member. The arcuate ridges have a predetermined length so as to engage the bosses on the clamp ring upon rotation of the flow control member in opposite directions to align the transverse bore in the flow control member with the transverse bore in the body. In addition, a projection is formed on each boss and engage recesses formed in the end of the flow control member when the flow control member is rotated to a valve closed position to frictionally define the valve closed position.

In another embodiment, a second transverse bore is formed in the flow control member and angularly spaced from the first transverse bore. The arcuate ridges of the rotation limiting means are modified to permit the flow control member to be rotated between the first position in which the first transverse bore is aligned with and disposed in fluid flow communication with the transverse bore in the body, a third position in which the second transverse bore is aligned and disposed in fluid flow communication with the transverse bore in the body, and the second position intermediate the first and third positions in which the flow control member closes off the transverse bore in the body.

The valve of the present invention enables minute quantities of gas stored in a sealed container to be easily withdrawn from the container or additional gas or other fluids to be injected into the container without permitting the discharge of large quantities of the gas from the container. The septum in the valve of the present invention is displaced from the main fluid flow path through the valve and does not form part of the flow control function provided by the valve.

The valve of the present invention is easily rotatable between an open and closed positions to form the fluid flow path or to block the fluid flow path through the valve and the interior chamber of the sealed container. Alternately, a second transverse bore may be formed in the fitting body to provide a second flow path through the valve. The valve of the present invention is also easily mountable on a gas sample container formed with expandable side walls. In addition, the valve of the present invention may be easily disassembled for remounting on another sealed container or for cleaning and/or replacement of various components thereof for reuse of the valve.

BRIEF DESCRIPTION OF THE DRAWING

The various features, advantages and other uses of the present invention will become more apparent by referring to the following detailed description and drawing in which.

DESCRIPTION OF THE PREFERRED EMBODIMENTS

The present invention is a valve which is attachable to a sealed container and which controls the flow of fluid, such as gas, into and out of the container. Although the valve of the present invention may be employed with a variety of different types of containers, the following description and drawings will describe the valve of the present invention as being employed with an expandable gas sample container, by way of example only.

As is conventional, a gas sample container 10 is connectible to a gas source to collect and temporarily store a gas sample. The container 10, after disconnection from the gas source, can be used to store the gas samples for any length of time before all or a predetermined quantity of the stored gas is removed from the container and supplied to suitable test equipment, not shown, for testing and/or analysis.

Figure 1:
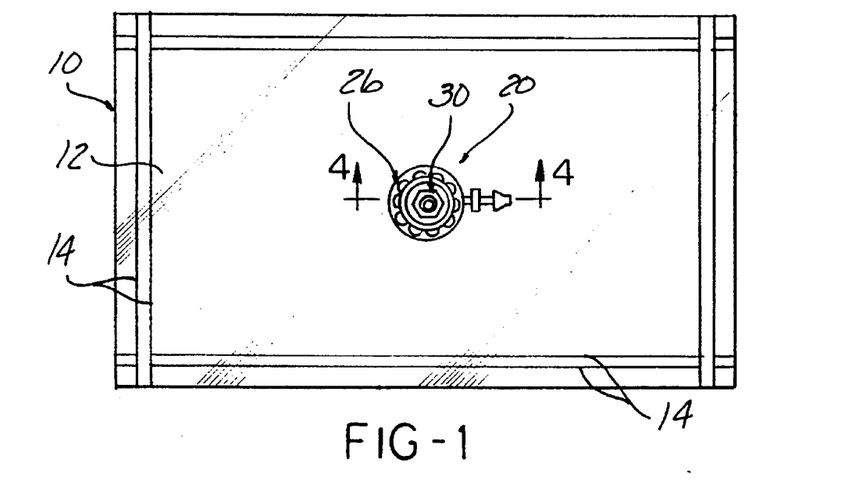
FIG. 1 is a plan view of a gas emission sample container having a valve constructed in accordance of the teachings of the present invention mounted thereon.

As shown in FIG. 1, the gas sample container 10 comprises a sealed enclosure of any shape, such as rectangular, square, circular, etc. It will be understood that a rectangular shape for the container 10 is illustrated by way of example only. Further, the container 10 may be provided in different sizes depending upon the requirements of a particular test.

The sealed, expandable container or bag 10 is typically formed of at least two flexible sheets of chemically inert material. Preferably, fluorinated plastics chosen from the fluorocarbon family, such as those sold under the trademarks TEFLON, TEDLAR and HALAR, may be employed. The sealed container 10 is typically formed of front and back sheets, with only front sheet 12 being shown in FIG. 1. The front sheet 12 and the back sheet may be formed of a single thickness or ply, typically two or four mils. in thickness. Double ply sheets to form the front and back of the sealed container 10 may also be employed.

The front and back sheets are sealingly connected at their peripheral edges by any suitable means, such as by heat seams 14. For additional sealing capability, two spaced heat seams 14 may be formed about the entire peripheral edges of the front sheet 12 and the back sheet of the sealed container 10. The seam or seams 14 seal the peripheral edges of the front sheet 12 to the back sheet and form a hollow, expandable, internal cavity within the interior of the sealed container 10.

Figure 4:
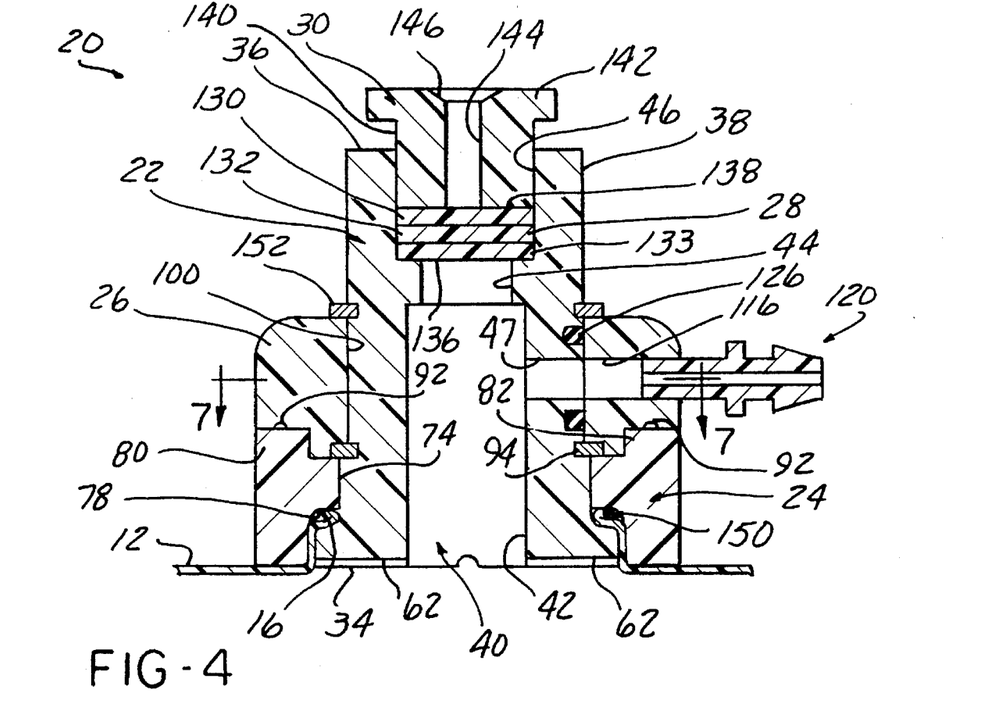
FIG. 4 is a cross sectional view of the valve generally taken along line 4—4 in FIG. 1.

As shown in FIG. 4, an aperture 16 is formed approximately centrally on the front sheet 12 and opens to the interior cavity or chamber within the sealed container 10. Optionally, a thin reinforcing member, such as a reinforcing strip or tape, not shown, may be adhesively mounted on the front sheet 12 surrounding the aperture 16. In the event that the reinforcing strip is used, a corresponding aperture is formed in the reinforcing strip in alignment with the aperture 16 in the front sheet 12 of the container 10.

A valve 20 constructed in accordance with the teachings of the present invention is sealingly mounted on the container 10 in communication with the aperture 16 in the front sheet 12 of the container 10 as shown in FIGS. 1 and 4. The valve 20 is operative to control the flow of a fluid, such as gas, into and out of the interior chamber within the sealed container 10.

According to the present invention, the valve 20, as shown in FIGS. 2–8, is formed of a fitting body 22, a clamp ring 24, a flow control member or valve ring 26, a septum 28 and a septum retainer 30. All of the components of the valve 20, including the fitting body 22, the clamp ring 24, the valve ring 26 and the septum retainer 30 are preferably formed of a chemically inert material, such as polypropylene, nylon or materials sold under trademarks KYNAR or PFA TEFLON. Alternately, at least the fitting body 22, and optionally, the valve ring 26, may be formed of a chemically inert material, with the remaining components of the valve 20 being formed of other, compatible materials. In a more preferred embodiment, the materials used to form the components of the valve 20 are chosen to match the material used to form the sealed container 10.

Figure 2:
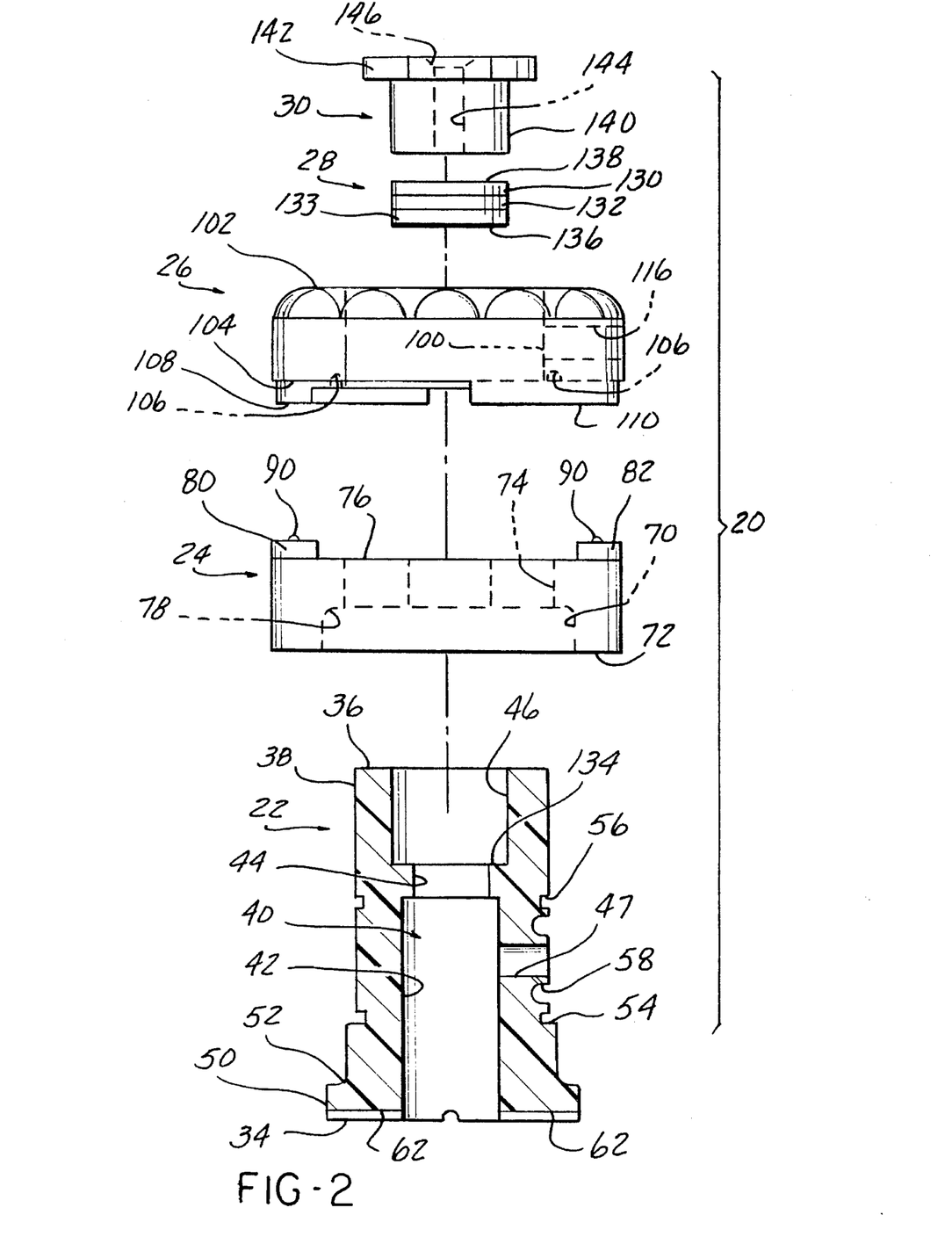
FIG. 2 is an exploded, side elevational view of the valve of the present invention.
Figure 8:
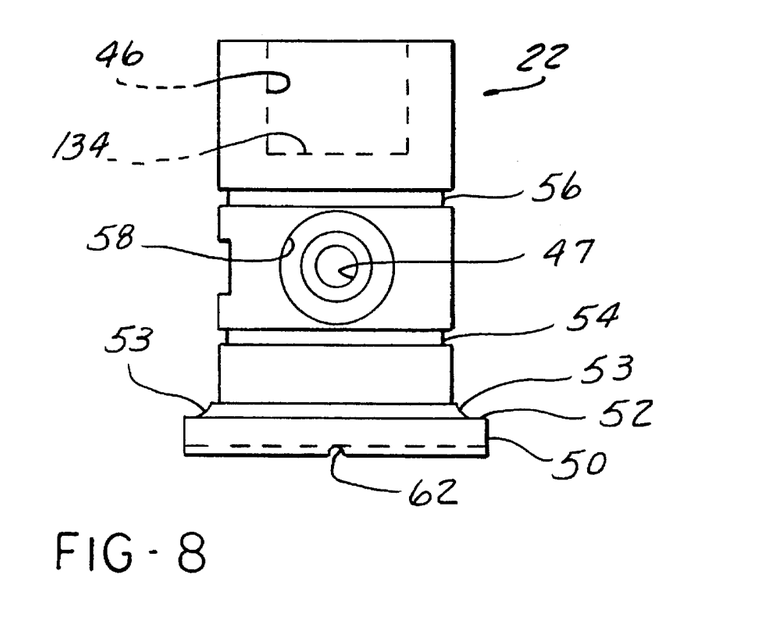
FIG. 8 is a right side elevational view of the fitting body shown in FIG. 2.

As shown in FIGS. 2, 4 and 8, the fitting body 22 has a generally elongated, cylindrical shape with opposed first and second ends 34 and 36 and a side wall 38. A through bore 40 extends through the fitting body 22 and opens through the first end 34 and the second end 36 of the fitting body 22. The through bore 40 is formed of a first bore portion 42 of a first diameter which extends for a predetermined distance from the first end 34 of the fitting body 22, a second or intermediate bore portion 44 of smaller diameter which extends from one end of the first bore portion 42, and a third bore portion 46 which extends from the second or intermediate bore portion 44 to an open end at the second end 36 of the fitting body 22. The third bore portion 46 has a larger diameter than the second or intermediate bore portion 44. A transverse bore 47 extends through the side wall 38 into fluid flow communication with the first portion 42 of the through bore 40.

An enlarged collar 50 is formed at the first end 34 of the fitting body 22 and has a larger diameter than the outer diameter of the side wall 38 of the fitting body 22. A shoulder 52 is formed at the juncture of the collar 50 and a bottom portion of the side wall 38. A pair of spaced flats 53, shown in FIG. 8, are formed in the bottom portion of the side wall 38 to form a positioning means for the clamp ring 24.

A first annular recess or groove 54 is formed on the exterior of the side wall 38 of the fitting body 22 spaced from the shoulder 52. The recess 54 is sized to receive a retaining ring, as described hereafter. A second retaining ring receiving recess or groove 56 is also formed on the exterior surface of the side wall 38 and is spaced from the first retaining ring receiving recess or groove 54. In addition, an annular groove 58 is formed in the exterior surface of the side wall 38 between the first and second retaining ring receiving grooves 54 and 56 and concentrically surrounds the outer end of the transverse bore 47. The groove 58 is designed to receive an O-ring, as also described in greater detail hereafter.

Figures 3, 7:
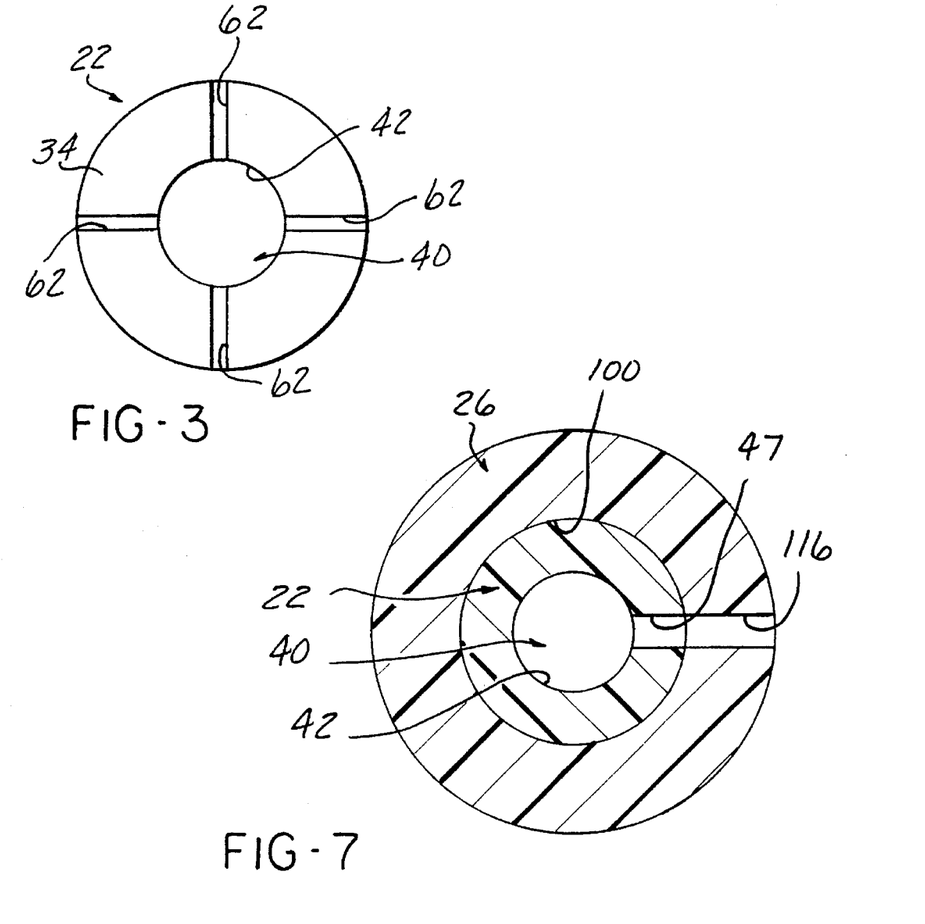
FIG. 3 is a bottom plan view of the fitting body of the valve shown in FIG. 2.
FIG. 7 is a cross sectional view generally taken along line 7—7 in FIG. 4, showing valve in the open position with the fitting not shown.

As shown in FIGS. 2, 4 and 8, and in greater detail in FIG. 3, at least one and preferably a plurality, such as four, circumferentially spaced, radially extending slots 62 are formed in the first end 34 of the fitting body 22. Each of the slots 62 is disposed in communication with the open end of the first bore portion 42 of the bore 40 extending through the fitting body 22 to provide radially extending fluid flow paths for gas flow into and out of the bore 40 as will be described in greater detail hereafter.

As shown in FIGS. 2, 4, 5 and 6, the clamp ring 24 is in the form of a cylindrical body having a first, larger diameter bore 70 extending from a first end 72 and a smaller diameter bore 74 coaxially aligned with and communicating with the first bore 70 and extending from the first bore 70 to a second end 76 of the clamp ring 24. An internal shoulder 78 is formed at the juncture of the first and second bores 70 and 74, respectively, which engages the shoulder 52 on the first end of the fitting body 22 when the clamp ring 24 is mounted on the fitting body 22. The second bore 74 is sized to slide over the side wall 38 of the fitting body 22 in a close fit. The second bore 74 is preferably formed of arcuate end portions 84 and 86 which are interconnected by straight side wall portions 88 and 89. The straight side wall portions 88 and 89 align with the flats 53 on the fitting body 22 to properly align the clamp ring 24 on the fitting body 22.

Figure 5:
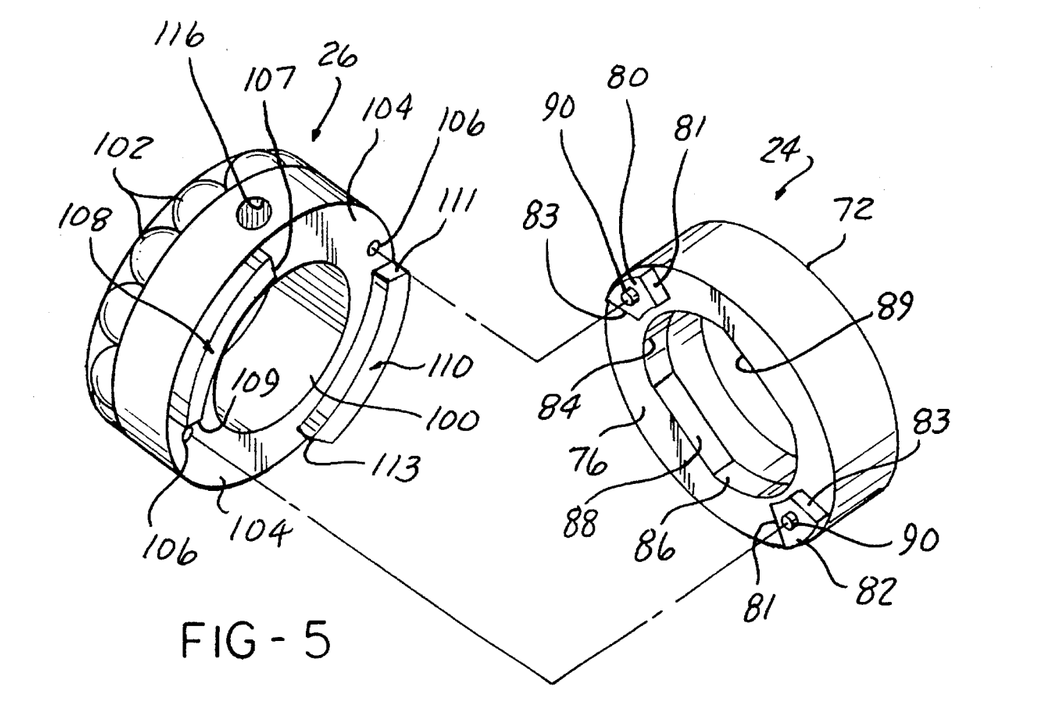
FIG. 5 is an exploded, perspective view of the valve ring and clamp ring of the valve shown in FIG. 2.
Figure 6:
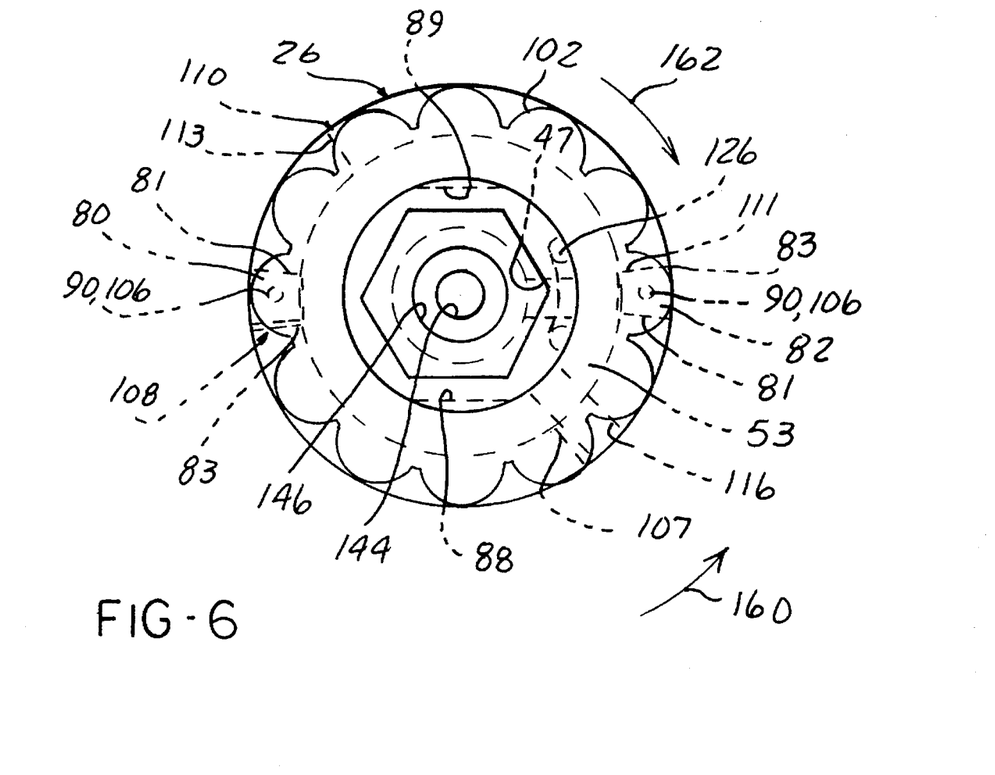
FIG. 6 is an enlarged plan view of the valve of the present invention, shown in the closed position with the fitting not shown.

A pair of diametrically opposed bosses 80 and 82 extend upward from the second end 76 of the clamp ring 24. The bosses 80 and 82 are located at the periphery of the clamp ring 24 as shown in FIGS. 2, 5 and 6, and each have opposed side faces 81 and 83. A raised projection 90 is formed on each boss 80 and 82 and extends outward therefrom. The projections 90 interact with suitably formed recesses or detents on the valve ring 26 as will be described hereafter.

A retaining means, such as a snap ring 94, shown in FIG. 4, is inserted into the first groove 54 on the fitting body 22 after the clamp ring 24 has been mounted over the fitting body 22 with the shoulder 78 disposed in close proximity or engagement with the shoulder 52 on the fitting body 22. The retainer or snap ring 94 securely retains the clamp ring 24 on the fitting body 22.

The valve ring 26, as shown in FIGS. 2 and 4–7 also has a generally cylindrical, annular shape with an axially extending through bore 100 extending between opposite ends thereof. A suitably formed finger gripping surface, preferably in the form of circumferentially spaced, generally hemispherical-shaped projections 102, is formed on one end of the valve ring 26 to provide a suitable gripping surface to enable easy rotation of the valve ring 26 about the fitting body 22 as described hereafter.

A first end 104 of the valve ring 26 has a pair of recesses or detents 106 formed therein. The recesses 106 are circumferentially spaced apart about the first end 104 of the valve ring 26 and are located to engage the projections 90 on the clamp ring 24 as the valve ring 26 is rotated to a closed position, as described hereafter.

A pair of circumferentially spaced, arcuate shaped ridges 108 and 110 are formed on the valve ring 26 and extend axially outward from the first end 104 as shown in FIGS. 2 and 5. The ridges 108 and 110 have a predetermined arcuate length and terminate in end faces 107 and 109 on ridge 108 and end faces 111 and 113 on ridge 110. The ridges 108 and 110 slidably engage the second end 76 of the clamp ring 24. When the valve ring 26 is mounted on the clamp ring 24, the arcuate ridges 108 and 110 on the valve ring 26 are disposed between the bosses 80 and 82 on the clamp ring 24 and control the amount of rotation of the valve ring 26 with respect to the clamp ring 24 as will be described in greater detail hereafter.

As shown in FIGS. 2, and 4–8, at least a first transversely extending bore 116 extends through a side wall of the valve ring 26. The first bore 116 is designed to be moved upon rotation of the valve ring 26 into and out of fluid flow communication with the transverse bore 47 in the fitting body 22.

As shown in FIG. 4, a suitable fitting or coupling 120 is mounted in an outer end of the bore 116 to provide a connection to an external conduit, not shown, to form a fluid flow path between the valve 20 and an external gas source, or to test equipment for receiving gas stored within the container 10. For example, the fitting 120 may comprise a suitably formed leur fitting which is fixedly mounted in one end of the bore 116 by means of a press fit between a tapered end of the fitting 120 and the preferably tapered bore 116. The opposite end of the fitting 120 is sized to engage an external conduit, not shown. Different fittings 120, each with the same size tapered end and a different diameter outer end may be inserted into the bore 116 to permit connection to different diameter conduits.

As shown in FIG. 4, an O-ring 126 is mounted in the groove 58 in the fitting body 22. The O-ring 126 surrounds the outer end of the bore 47 in the fitting body 22. The O-ring 126 forms a seal around the fluid flow path formed between the bore 116 and the bore 47. In addition, when the valve ring 26 is rotated to the closed position, as described hereafter, in which the bore 116 is displaced from and not in fluid flow communication with the transverse bore 47 in the fitting body 22, the O-ring 126 forms a seal between the valve ring 26 and the fitting body 22 to close the valve 20 to gas flow and to seal the gas in the attached container 10.

As shown in FIGS. 2 and 4, a septum 28 is mountable in the third bore portion 46 of the fitting body 22. The septum 28 may be formed of any suitable self-healing material which may be pierced by a syringe or other sharp instrument, while still providing a seal when the syringe is removed therefrom. By way of example only, the septum 28 is formed of first and second annular disks 130 and 132, each formed of silicone. The disks 130 and 132 may be joined together by means of an adhesive. It will be understood that the septum 28 may also be formed of a single disk or material layer of silicone or other self-healing material. A third disk or layer 133 is bonded to or formed on the second bore position 44 side of the disk 132. The third disk 133 is formed of a chemically inert material, such as TEFLON, since it contacts the gas in the second bore position 44.

As shown in FIGS. 2 and 4, the septum 28, when mounted in the end 134 of the third bore portion 46 in the fitting body 22, has a first surface 136 facing the second bore portion 44 in the fitting body 22. However, this surface 136 is spaced from the transverse bore 47 in the fitting body 22 so as not to be in the main flow path between the container 10, the first bore portion 42, the transverse bore 47 in the fitting body 22, and the bore 116 in the valve ring 26. The septum 28 also has a second opposed surface 138 which faces away from the first bore portion 42 in the fitting body 22.

The septum retainer 30 is also mounted in the third bore portion 46 in the fitting body 22 in a releasable interference or press fit. The septum retainer 30 may have any suitable shape. By way of example only, the septum retainer 30 has a generally cylindrical body portion 140 which is sized to engage the third bore portion 46 in the fitting body 22 in a press fit and to compress the septum 28 into sealing engagement with one end of the third bore portion 46. An enlarged end flange 142 is integrally formed with the cylindrical body portion 140 and extends exteriorly of the second end 36 of the fitting body 22 as shown in FIG. 4. By example only, the end flange 142 has a hex shape with peripheral flats.

A longitudinally extending bore 144 is formed through the septum retainer 30 and opens to the second surface 138 of the septum 28. The exterior end portion 146 of the bore 144 may be outwardly tapered as shown in FIGS. 2 and 4. The bore 144 serves as an entry path for a syringe or other sharp instrument which can pierce the septum 28 and withdraw or inject minute quantities of gas from or into the sealed container 10 through the bore 40 in the fitting body 20 without interrupting the operation of the valve 20 in controlling the insertion and discharge of large quantities of gas to and from the container 10. The bore 144 preferably has a diameter significantly larger than the O.D. of a syringe to enable a choice of piercing locations on the septum 28.

In assembling the valve 20 of the present invention, as shown in FIGS. 2 and 4, the fitting body 22 is first inserted through the aperture 16 in the front sheet 12 of the container 10, with the edges of the front sheet 12 bounding the aperture 16 being disposed in registry with the shoulder 52 on the fitting body 22 as shown in FIG. 4. An O-ring 150 is inserted over the side wall 38 of the fitting body 22 into sealing engagement with the peripheral edges of the sheet 12 bounding the aperture 16 to provide a complete seal about the aperture 16. The clamp ring 24 is then inserted over the fitting body 22 with the side wall portions 88 and 89 aligned with the flats 53 on the fitting body 22 until the shoulder 78 in the clamp ring 24 engages the shoulder 52 and the O-ring 150. The snap ring 94 is then inserted into the first groove 54 on the fitting body to hold the clamp ring 24 in position on the fitting body 22 and to compress the O-ring 150 onto the shoulder 52 on the fitting body 22 into sealing engagement with the sheet 12.

Next, the valve ring 26 is inserted over the fitting body 22 into engagement with the clamp ring 24. During such insertion, the valve ring 26 is properly oriented with respect to the clamp ring 24 so as to place the annular ridges 108 and 110 on the valve ring 26 in a slidingly movable position between the bosses 80 and 82 on the clamp ring 24. A snap ring 152, shown in FIG. 4, is inserted into the groove 56 in the fitting body 22 to retain the valve ring 26 in a fixed axial position on the fitting body 22; while still permitting rotation of the valve ring 26 about a longitudinal axis extending through the fitting body 22. The septum 28 and septum retainer 30 are then inserted into the third bore portion 46 in the fitting body 22. It should be noted that the septum 28 and septum retainer 30 may also be inserted into the fitting body 22 prior to the mounting of the valve ring 26 on the fitting body 22. Finally, a suitable fitting 120 is mounted in the bore 116 in the valve ring 26.

In operation, with the valve 20 assembled as described above, and mounted on a completely evacuated container 10, the fitting 120 may be connected to a suitable conduit which in turn is connected to a source of fluid, such as a source of gas, or to test equipment. It should be noted that prior to filling the container 10 with the gas emissions, the valve ring 26 is rotated in the direction of arrow 162 in FIG. 6 to a closed position such that the transverse bore 116 is displaced from and not aligned with the transverse bore 47 in the fitting body 22. In this position, the projections 90 engage the detents 106 to frictionally hold the valve ring 26 in a closed position on the fitting body 22. Also, in the position, the O-ring 126 sealingly engages the inner face of the valve ring 26 to sealingly close the valve 20 to fluid flow therethrough.

Next, the valve ring 26 is rotated in the direction of arrow 160 in FIG. 6 from the closed position shown in FIG. 6 to a first open position shown in FIG. 7 in which the first transverse bore 116 in the valve ring 26 is aligned with the transverse bore 47 in the fitting body 22. The valve ring 26 is rotated in the direction of arrow 160 until the side face 107 of the annular ridge 108 on the valve ring 26 engages the side 81 of the boss 82 on the clamp ring 24. At the same time, the side face 113 of the opposite annular ridge 110 on the valve ring 26 engages the side face 81 of the opposite boss 80 on the clamp ring 24. The engagement of the side faces 107 and 113 of the annular ridges 108 and 110 with the sides 81 of the bosses 80 and 82 form a limit or stop which defines the first open position of the valve 20. This allows the flow of gas through the fitting 120, the aligned transverse bores 116 and 47, and the bore 40 in the fitting body 22 into the container 10. After a quantity of gas has been supplied to the container 10, the valve ring 26 is rotated in a direction opposite to arrow 160 to the closed position shown in FIG. 6 to block the flow path through the transverse bore 47 and the through bore 40 in the fitting body 22. The fitting 120 may then be disconnected from the gas source and the container 10 immediately transferred to suitable test equipment or merely stored for gas testing at a later date.

When it is desired to discharge the stored gas from the container 10 for testing or to completely evacuate the container 10, the fitting 120 mounted in the first bore 116 in the valve ring 26 is connected to a suitable conduit on such test or evacuation equipment. The valve ring 26 is then rotated to the open position described above and shown in FIG. 7 to form a fluid flow path from the interior chamber of the container 10 through the bore 40 and the transverse bore 47 in the fitting body 22, the first transverse bore 116 in the valve ring 26 and the fitting 120. It should be noted that during such evacuation of gas from the container 10, the radially extending slots 62 at the first end 34 of the fitting body 22 ensure that the bag is completely evacuated of all gaseous contents. The slots 62 prevent the surrounding portion of the back sheet of the container 10 from engaging and closing off the opening to the bore 40 in the valve 20 which could possibly trap a portion of the gas within the container 10.

At any time when the valve 20 is in the closed position shown in FIG. 6, a syringe may be inserted into the bore 144 in the septum retainer 30 through the septum 28 and into the first bore portion 42 in the bore 40 in the fitting body 22 to inject gas into the sealed container 10 on which the valve 20 is mounted or to withdraw minute quantities of gas from the sealed container 10. Upon withdrawal of the syringe from the septum 20, the self-healing characteristics of the septum 20 immediately close off the opening formed in the septum 28 by the syringe to again completely seal off the bore 40 in the fitting body 22. It should be noted that the large diameter of the bore 144 and the septum retainer 30 provides multiple locations for the syringe to pierce the septum 28. This prolongs the useful life of the septum 28 since the same location on the septum 28 is not repeatedly pierced by the syringe.

Figure 9:
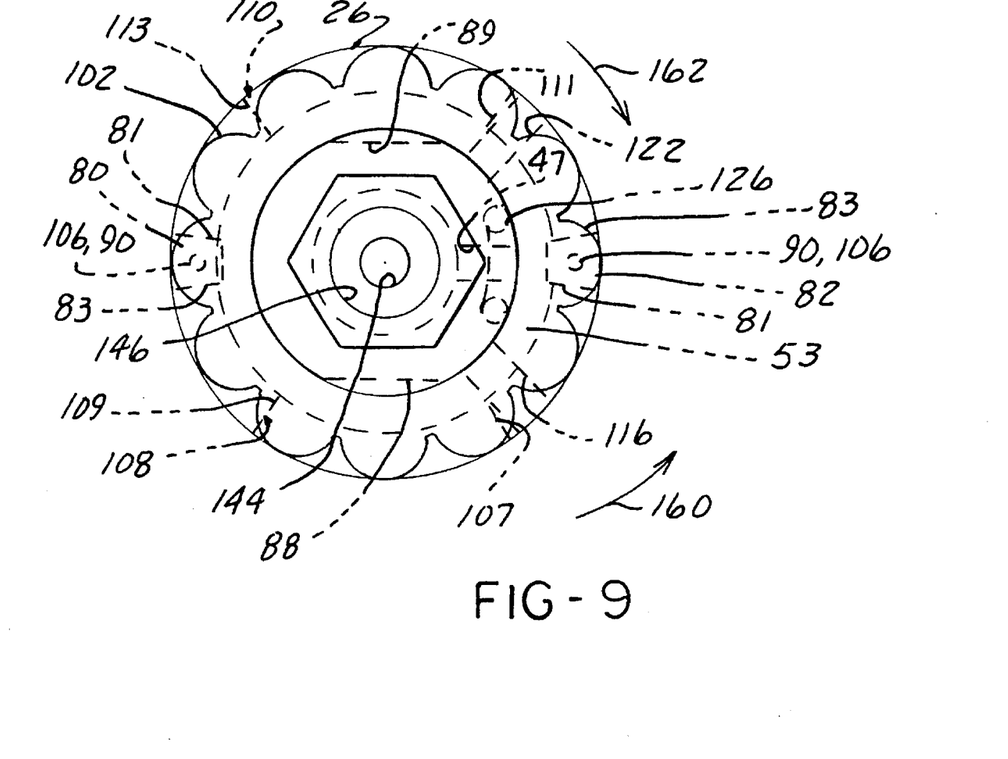
FIG. 9 is an enlarged plan view of another embodiment of the valve of the present invention, with the fitting not shown.

An optional second transverse bore 122 may also be formed in the valve ring 26, as shown in FIG. 9. The second transverse bore 122 is spaced a predetermined circumferential distance from the first transverse bore 116, such as 90° from the first transverse bore 116. For example, the first bore 116, with a suitably mounted fitting 120 therein, may be employed for supplying gas through the valve 20 to the container 10; while the second transverse bore 122, also with a suitably formed fitting 120 mounted therein, may be employed to separately discharge gas from the container 10 to external test equipment, etc. The second transverse bore 122 can also be employed to inject a gas or other fluid into the sealed container 10 for reaction with the contents of the container 10.

In this embodiment, the arcuate length of the ridges 108 and 110 on the valve ring 26 are shortened from that shown in FIG. 5 to permit the full rotation of the valve ring 26 to a third position in which the second transverse bore 122 is aligned with and disposed in fluid flow communication with the transverse bore 47 in the body 22.

For discharge of gas from or the injection of gas into the container 10 through the second bore 122, the valve ring 26 can be rotated in the direction of arrow 162 shown in FIG. 6 to the third position in which the second transverse bore 122 is aligned with and disposed in fluid flow communication with the transverse bore 47 in the fitting body 22 to form a fluid flow path to the container 10 through the valve 20. During such rotation, the side faces 109 and 111 of the annular ridges 108 and 110, respectively, engage the side faces 83 of the bosses 80 and 82 on the clamp ring 24 to limit or stop rotation of the valve ring 26 at the third position of the valve ring 20. When gas flow through the valve 20 is to be terminated, the valve ring 26 is rotated back to the closed position shown in FIG. 6.

In summary, there has been disclosed a unique valve which allows withdrawal and/or injection of minute quantities of gas or fluid from or to a sealed container to which the valve is attached without requiring a full opening of the valve. The present valve is easily mounted on a sealed container and, particularly, a sealed expandable container having flexible side walls, such as a gas sample container. Further, since the septum in the present valve is located out of the main flow path through the valve, the valve may be repeatedly opened and closed without causing wear on the septum. In addition, the unique construction of the valve of the present invention enables the valve to be easily disassembled and removed from a sealed container for cleaning, replacement of worn parts and reuse on the same or a different sealed container. This prolongs the useful life of the valve of the present invention and reduces the overall cost of using such a valve with a sealed container. The present valve is also constructed with a plurality of separate flow bores which enables separate gas flow connections to be provided on the valve.

What is claimed is:

1. A fluid valve comprising:

a body with a fluid flow bore extending therethrough, the bore having first and second open ends;

a transverse bore formed in the body disposed in fluid flow communication with the fluid flow bore;

a flow control member mounted on the body and having a first transverse bore extending therethrough, the flow control member being movable between a first position in which the first transverse bore in the flow control member is aligned with the transverse bore in the body for fluid flow therethrough, and a second position in which the first transverse bore in the flow control member is offset from the transverse bore in the body to close off fluid flow through the first end of the fluid flow bore in the body; and a septum mounted in the second end of the fluid flow bore in the body and displaced from a fluid flow path between the transverse bore and the first end of the fluid flow bore in the body, the septum having a first surface facing and sealingly closing the second end of the fluid flow bore in the body.

2. The valve of claim 1 further comprising:

the flow control member being rotatably mounted on the body; and means for limiting rotational movement of the flow control member between the first and second positions.

3. The valve of claim 1 wherein:

the flow control member comprises an annular member rotatably mounted about the body.

4. The valve of claim 1 wherein the flow control member further comprises:

a second transverse bore formed therein circumferentially spaced from the first transverse bore.

5. The valve of claim 1 further comprising:

means for mounting the flow control member on the body for rotational movement with respect to the body while preventing axial movement of the flow control member with respect to the body.

6. A fluid valve comprising:

a body with a fluid flow bore extending therethrough, the bore having first and second open ends;

a transverse bore formed in the body disposed in fluid flow communication with the fluid flow bore;

a flow control member mounted on the body and having a first transverse bore extending therethrough, the flow control member being movable between a first position in which the first transverse bore in the flow control member is aligned with the transverse bore in the body for fluid flow therethrough, and a second position in which the first transverse bore in the flow control member is offset from the transverse bore in the body to close off fluid flow through the first end of the fluid flow bore in the body;

a septum mounted in the second end of the fluid flow bore in the body and displaced from a fluid flow path between the transverse bore and the first end of the fluid flow bore in the body, the septum having a first surface facing and sealingly closing the second end of the fluid flow bore in the body; and means for mounting the flow control member on the body for rotational movement with respect to the body while preventing axial movement of the flow control member with respect to the body, the mounting means including a retaining ring receiving groove formed on the body, and a retaining ring mounted in the retaining ring receiving groove for axially fixedly mounting the flow control member on the body.

7. A fluid valve comprising:

a body with a fluid flow bore extending therethrough, the bore having first and second open ends;

a transverse bore formed in the body disposed in fluid flow communication with the fluid flow bore;

a seal receiving groove formed on the body concentrically surrounding an outer end of the transverse bore in the body;

a seal member mounted in the seal receiving groove;

a flow control member mounted on the body and having a first transverse bore extending therethrough, the flow control member being movable between a first position in which the first transverse bore in the flow control member is aligned with the transverse bore in the body for fluid flow therethrough, and a second position in which the first transverse bore in the flow control member is offset from the transverse bore in the body to close off fluid flow through the first end of the fluid flow bore in the body; and a septum mounted in the second end of the fluid flow bore in the body and displaced from a fluid flow path between the transverse bore and the first end of the fluid flow bore in the body, the septum having a first surface facing and sealingly closing the second end of the fluid flow bore in the body.

8. The valve of claim 7 wherein the seal member comprises an O-ring.

9. The valve of claim 1 further comprising:

means for mounting the body on a sealed container having an aperture disposed in fluid flow communication with the first end of fluid flow bore in the body.

10. A fluid valve comprising:

a body with a fluid flow bore extending therethrough, the bore having first and second open ends;

means for mounting the body on a sealed container having an aperture disposed in fluid flow communication with the first end of the fluid flow bore in the body, the mounting means including an annular clamp member mounted on one end of the body and means for fixedly mounting the clamp member on the body;

a transverse bore formed in the body disposed in fluid flow communication with the fluid flow bore;

a flow control member mounted on the body and having a first transverse bore extending therethrough, the flow control member being movable between a first position in which the first transverse bore in the flow control member is aligned with the transverse bore in the body for fluid flow therethrough, and a second position in which the first transverse bore in the flow control member is offset from the transverse bore in the body to close off fluid flow through the first end of the fluid flow bore in the body; and a septum mounted in the second end of the fluid flow bore in the body and displaced from a fluid flow path between the transverse bore and the first end of the fluid flow bore in the body, the septum having a first surface facing and sealingly closing the second end of the fluid flow bore in the body.

11. The valve of claim 10 wherein the means for fixedly mounting the clamp member on the body comprises:

a retaining ring receiving groove formed on the body; and a retaining ring mounted in the retaining ring receiving groove for axially fixedly mounting the clamp member on the body.

12. The valve of claim 10 further comprising:

an annular shoulder formed on the one end of the body;

the clamp member sealingly engaging edges of the sealed container surrounding the aperture in the sealed container to the annular shoulder on the body.

13. The valve of claim 12 further comprising:

a seal member disposed between the annular shoulder on the body and the clamp member.

14. A fluid valve comprising:

a body with a fluid flow bore extending therethrough, the bore having first and second open ends;

at least one groove formed in an end of the body and extending radially from the first open end of the fluid flow bore in the body;

a transverse bore formed in the body disposed in fluid flow communication with the fluid flow bore;

a flow control member mounted on the body and having a first transverse bore extending therethrough, the flow control member being movable between a first position in which the first transverse bore in the flow control member is aligned with the transverse bore in the body for fluid flow therethrough, and a second position in which the first transverse bore in the flow control member is offset from the transverse bore in the body to close off fluid flow through the first end of the fluid flow bore in the body; and a septum mounted in the second end of the fluid flow bore in the body and displaced from a fluid flow path between the transverse bore and the first end of the fluid flow bore in the body, the septum having a first surface facing and sealingly closing the second end of the fluid flow bore in the body.

15. The valve of claim 1 further comprising:

means for retaining the septum in the fluid flow bore in the body.

16. A fluid valve comprising:

a body with a fluid flow bore extending therethrough, the bore having first and second open ends;

a transverse bore formed in the body disposed in fluid flow communication with the fluid flow bore;

a flow control member mounted on the body and having a first transverse bore extending therethrough, the flow control member being movable between a first position in which the first transverse bore in the flow control member is aligned with the transverse bore in the body for fluid flow therethrough, and a second position in which the first transverse bore in the flow control member is offset from the transverse bore in the body to close off fluid flow through the first end of the fluid flow bore in the body;

a septum mounted in the second end of the fluid flow bore in the body and displaced from a fluid flow path between the transverse bore and the first end of the fluid flow bore in the body, the septum having a first surface facing and sealingly closing the second end of the fluid flow bore in the body; and means for retaining the septum in the fluid flow bore in the body, the retaining means including:
   a retainer mounted in the second end of the fluid flow bore in the body in engagement with the septum; and
   a through bore having first and second open ends and extending through the retainer, one of the first and second open ends facing the septum.

17. The valve of claim 16 wherein:

the other of the first and second ends of the through bore in the retainer has inwardly tapering side walls extending between a larger diameter outer end and a smaller diameter inner end opening to the through bore in the retainer.

18. A fluid valve comprising:

a body with a fluid flow bore extending therethrough, the bore having first and second open ends;

a transverse bore formed in the body disposed in fluid flow communication with the fluid flow bore;

a flow control member mounted on the body and having a first transverse bore extending therethrough, the flow control member being movable between a first position in which the first transverse bore in the flow control member is aligned with the transverse bore in the body for fluid flow therethrough, and a second position in which the first transverse bore in the flow control member is offset from the transverse bore in the body to close off fluid flow through the first end of the fluid flow bore in the body;

a septum mounted in the second end of the fluid flow bore in the body and displaced from a fluid flow path between the transverse bore and the first end of the fluid flow bore in the body, the septum having a first surface facing and sealingly closing the second end of the fluid flow bore in the body;

the flow control member rotatably mounted on the body;

means for limiting rotational movement of the flow control member between the first and second positions; and a clamp member disposable over the body for attaching the body to a container;

the means for limiting rotational movement of the flow control member including:

a first projection formed on and extending from the clamp member;

a second projection formed on and extending from the flow control member;

the flow control member rotatably mounted on the body such that the second projection on the flow control member engages the first projection on the clamp member and stops rotation of the flow control member in the first position.

19. The valve of claim 18 wherein:

the first projection includes a pair of circumferentially spaced projections formed on the clamp member;

the second projection includes a pair of circumferentially spaced projections on the flow control member;

each one of the pair of second projections engaging one of the pair of first projections when the flow control member is rotated to the first position.

20. The valve of claim 18 further comprising:

mating detent means, formed on the clamp member and the flow control member and circumferentially spaced from the first and second projections, for frictionally retaining the flow control member in the second position upon rotation of the flow control member.

21. The valve of claim 18 further comprising:

mating positioning means, formed on the body and the clamp member, for positioning the clamp member on the body for mating engagement of the first and second projections.

22. The valve of claim 1 wherein:

the septum is formed of a disk formed of a self-healing material.

23. A fluid valve comprising:

a body with a fluid flow bore extending therethrough, the bore having first and second open ends;

a transverse bore formed in the body disposed in fluid flow communication with the fluid flow bore;

a flow control member mounted on the body and having a first transverse bore extending therethrough, the flow control member being movable between a first position in which the first transverse bore in the flow control member is aligned with the transverse bore in the body for fluid flow therethrough, and a second position in which the first transverse bore in the flow control member is offset from the transverse bore in the body to close off fluid flow through the first end of the fluid flow bore in the body; and a septum mounted in the second end of the fluid flow bore in the body and displaced from a fluid flow path between the transverse bore and the first end of the fluid flow bore in the body, the septum having a first surface facing and sealingly closing the second end of the fluid flow bore in the body, the septum formed of a disk of a self-healing material, a chemically inert material layer disposed on the self-healing material disk and facing the first end of the fluid flow bore in the body.

24. The valve of claim 23 wherein the chemically inert material layer comprises:

a disk formed of a chemically inert material bonded to the self-healing material disk.

25. A fluid valve comprising:

a body having a through bore with first and second ends, the through bore extending through the body;

a transverse bore formed in the body and disposed in fluid flow communication with the through bore in the body between the first and second ends of the through bore;

a flow control member mounted on the body and having a first transversely extending bore formed therein, the flow control member being movable between a first position in which the first transverse bore is aligned with and disposed in fluid flow communication with the transverse bore and the through bore in the body for fluid flow therethrough, and a second position in which the first bore is offset from the transverse bore in the body to close off fluid flow through the through bore in the body;

clamp means mounted on one end of the body, for releasably clamping the body on a sealed container, with the through bore in the body disposed in fluid flow communication with a sealed container through an aperture in a side wall of the container;

a septum mounted in the second end of the through bore in the body and displaced from a fluid flow path between the transverse bore in the body and the first end of the through bore in the body, the septum having a first surface disposed in communication with the second end of the through bore in the body; and retaining means for sealingly retaining the septum in the second end of the through bore in the body.

26. The valve of claim 25 further comprising:

means for limiting rotational movement of the flow control element between the first and second positions.

27. The valve of claim 25 wherein:

the flow control member comprises an annular member rotatably mounted about the body.

28. The valve of claim 25 wherein the flow control member further comprises:

a second transverse bore, the second transverse bore circumferentially spaced from the first transverse bore.

29. The valve of claim 25 further comprising:

means for mounting the flow control member on the body for rotational movement with respect to the body while preventing axial movement of the flow control member with respect to the body.

30. The valve of claim 29 wherein the flow control member mounting means comprises:

a retaining ring receiving groove formed on the body; and a retaining ring mounted in the retaining ring receiving groove for axially fixedly mounting the flow control member on the body.

31. The valve of claim 25 further comprising:

a seal receiving groove formed on the body concentrically surrounding an outer end of the transverse bore in the body; and a seal member mounted in the seal receiving groove.

32. The valve of claim 31 wherein the seal member comprises an O-ring.

33. The valve of claim 25 further comprising:

a retaining ring receiving groove formed on the body; and a retaining ring mounted in the retaining ring receiving groove for axially fixedly mounting the clamp means on the body.

34. The valve of claim 33 further comprising:

an annular shoulder formed on the one end of the body;

the clamp means sealingly engaging edges of the sealed container surrounding the aperture in the sealed container to the annular shoulder on the body.

35. The valve of claim 34 further comprising:

a seal member disposed between the annular shoulder on the body and the clamp means.

36. The valve of claim 25 wherein:

the clamp means includes a clamp member disposable over the body for detachably mounting the body to a container;

the means for limiting rotational movement of the flow control member including:

a first projection formed on and extending from the clamp member;

a second projection formed on and extending from the flow control member;

the flow control member rotatably mounted on the body such that the second projection on the flow control member engages the first projection on the clamp member and stops rotation of the flow control member in the first position.

37. The valve of claim 36 wherein:

the first projection includes a pair of circumferentially spaced projections formed on the clamp member;

the second projection includes a pair of circumferentially spaced projections on the flow control member;

each one of the pair of second projections engaging one of the pair of first projections when the flow control member is rotated to the first position.

38. The valve of claim 36 further comprising:

mating detent means formed on the clamp member and the flow control member and circumferentially spaced from the first and second projections, for frictionally retaining the flow control member in the second position upon rotation of the flow control member.

39. The valve of claim 36 further comprising:

mating positioning means, formed on the body and the clamp member, for positioning the clamp member on the body for mating engagement of the first and second projections.

40. The valve of claim 25 wherein:

the septum is formed of a disk formed of a self-healing material.

41. The valve of claim 40 further comprising:

a chemically inert material layer disposed on the self-healing material disk and facing the first end of the through bore in the body.

42. The valve of claim 41 wherein the chemically inert material layer comprises:

a disk formed of a chemically inert material bonded to the self-healing material disk.

43. A gas sample apparatus for receiving and storing a quantity of gas comprising:

a sealed, expansible container formed of sealingly joined side walls, an aperture formed in and surrounded by portions of one of the side walls, the aperture opening to a hollow, expandable, interior chamber within the container;

a valve mounted on the container in fluid flow communication with an interior of the container through the aperture in the container, the valve including:

a body with a fluid flow bore extending therethrough, the bore having first and second open ends;

a transverse bore formed in the body disposed in fluid flow communication with the fluid flow bore;

a flow control member mounted on the body and having a first transverse bore extending therethrough, the flow control member being movable between a first position in which the first transverse bore in the flow control member is aligned with the transverse bore in the body for fluid flow therethrough, and a second position in which the first transverse bore in the flow control member is offset from the transverse bore in the body to close off fluid flow through the first end of the fluid flow bore in the body;

a septum mounted in the second end of the fluid flow bore in the body displaced from a fluid flow path between the transverse bore and the first end of the fluid flow bore in the body, the septum having a first surface facing and sealingly closing the second end of the fluid flow bore in the body; and means for sealingly mounting the valve to one of the side walls of the container with the first end of the fluid flow bore in the body of the valve disposed in fluid flow communication with the interior chamber within the container.

44. The gas sample container of claim 43 further comprising:

the flow control member being rotatably mounted on the body; and means for limiting rotational movement of the flow control member between the first and second positions.

45. The gas sample container of claim 43 wherein:

the flow control member comprises an annular member rotatably mounted about the body.

46. The gas sample container of claim 43 wherein the flow control member further comprises:

a second transverse bore formed therein circumferentially spaced from the first transverse bore.

47. The gas sample container of claim 43 further comprising:

means for mounting the flow control member on the body for rotational movement with respect to the body while preventing axial movement of the flow control member with respect to the body.

48. The gas sample container of claim 47 wherein the flow control member mounting means comprises:

a retaining ring receiving groove formed on the body; and a retaining ring mounted in the retaining ring receiving groove for axially fixedly mounting the flow control member on the body.

49. The gas sample container of claim 43 further comprising:

a seal receiving groove formed on the body concentrically surrounding an outer end of the transverse bore in the body; and a seal member mounted in the seal receiving groove.

50. The gas sample container of claim 49 wherein the seal member comprises an O-ring.

51. The gas sample container of claim 43 wherein the mounting means comprises:

an annular clamp member mounted about one end of the body; and means for fixedly mounting the clamp member on the body.

52. The gas sample container of claim 51 further comprising:

an annular shoulder formed on the one end of the body;

the clamp member sealingly engaging edges of the sealed container surrounding the aperture in the sealed container to the annular shoulder on the body.

53. The gas sample container of claim 52 further comprising:

an O-ring mounted between the annular shoulder on the body and the clamp member in sealing engagement with the edges of the container surrounding the aperture in the container.

54. The gas sample container of claim 43 further comprising:

at least one groove formed in the one end of the body and extending radially from one end of the fluid flow bore in the body.

55. The gas sample container of claim 43 further comprising:

means for retaining the septum in the fluid flow bore in the body.

56. The gas sample container of claim 55 wherein the retaining means comprises:

a retainer mounted in the second end of the fluid flow bore in the body in engagement with the septum; and a through bore having first and second open ends and extending through the retainer, one of the first and second open ends facing the septum.

57. The gas sample container of claim 56 wherein:

the other of the first and second ends of the through bore in the retainer has inwardly tapering side walls extending between a larger diameter outer end and a smaller diameter inner end opening to the through bore in the retainer.

58. The gas sample container of claim 51 wherein the means for fixedly mounting the clamp member on the body comprises:

a retaining ring receiving groove formed on the body; and a retaining ring mounted in the retaining ring receiving groove for axially fixedly mounting the clamp member on the body.

59. The gas sample container of claim 43 wherein:

the mounting means includes a clamp member disposable over the body for detachably mounting the body to the container;

the means for limiting rotational movement of the flow control member including:

a first projection formed on and extending from the clamp member;

a second projection formed on and extending from the flow control member;

the flow control member rotatably mounted on the body such that the second projection on the flow control member engages the first projection on the clamp member and stops rotation of the flow control member in the first position.

60. The gas sample container of claim 59 wherein:

the first projection includes a pair of circumferentially spaced projections formed on the clamp member;

the second projection includes a pair of circumferentially spaced projections on the flow control member;

each one of the pair of second projections engaging one of the pair of first projections when the flow control member is rotated to the first position.

61. The gas sample container of claim 59 further comprising:

mating detent means formed on the clamp member and the flow control member and circumferentially spaced from the first and second projections, for frictionally retaining the flow control member in the second position upon rotation of the flow control member.

62. The gas sample container of claim 59 further comprising:

mating positioning means, formed on the body and the clamp member, for positioning the clamp member on the body for mating engagement of the first and second projections.

63. The gas sample container of claim 43 wherein:

the septum is formed of a disk formed of a self-healing material.

64. The gas sample container of claim 63 further comprising:

a chemically inert material layer disposed on the self-healing material disk and facing the first end of the fluid flow bore in the body.

65. The gas sample container of claim 64 wherein the chemically inert material layer comprises:

a disk formed of a chemically inert material bonded to the self-healing material disk.

\* \* \* \* \*

UNITED STATES PATENT AND TRADEMARK OFFICE
CERTIFICATE OF CORRECTION

PATENT NO. : 5,456,126
DATED : October 10, 1995
INVENTOR(S) : James N. Suddath

It is certified that error appears in the above-indentified patent and that said Letters Patent is hereby corrected as shown below:

In the Abstract, line 13, delete "piercable" and inser --pierceable--.

Column 8, line 34, delete "position" and insert --portion--.

Column 8, line 36, delete "position" and insert --portion--.

Column 11, line 1, after "second" insert --transverse--.

Signed and Sealed this

Nineteenth Day of March, 1996

Attest:

BRUCE LEHMAN

Attesting Officer       Commissioner of Patents and Trademarks